United States Patent
Shan et al.

(10) Patent No.: US 11,045,537 B2
(45) Date of Patent: Jun. 29, 2021

(54) KLEBSIELLA PNEUMONIAE FROM MINKS AND ITS APPLICATION

(71) Applicant: Qingdao Agricultural University, Qingdao (CN)

(72) Inventors: Hu Shan, Qingdao (CN); Hongliang Zhang, Qingdao (CN); Ruimei Yang, Qingdao (CN); Chunyun Gai, Qingdao (CN); Xiaoming Song, Qingdao (CN); Tingting Zhang, Qingdao (CN)

(73) Assignee: QINGDAO AGRICULTURAL UNIVERSITY, Qingdao (CN)

( * ) Notice: Subject to any disclaimer, the term of this patent is extended or adjusted under 35 U.S.C. 154(b) by 0 days.

(21) Appl. No.: 16/943,836

(22) Filed: Jul. 30, 2020

(65) Prior Publication Data
US 2021/0030861 A1    Feb. 4, 2021

(30) Foreign Application Priority Data

Aug. 2, 2019   (CN) .......................... 201910713961X

(51) Int. Cl.
| | | |
|---|---|---|
| *A61K 39/108* | (2006.01) | |
| *A61K 39/39* | (2006.01) | |
| *C12R 1/22* | (2006.01) | |
| *A61K 39/00* | (2006.01) | |

(52) U.S. Cl.
CPC .......... *A61K 39/0266* (2013.01); *A61K 39/39* (2013.01); *C12R 1/22* (2013.01); *A61K 2039/552* (2013.01)

(58) Field of Classification Search
None
See application file for complete search history.

(56) References Cited

U.S. PATENT DOCUMENTS

2009/0068223 A1    3/2009    Meyers et al.

FOREIGN PATENT DOCUMENTS

| CN | 101360510 A | 2/2009 |
|---|---|---|
| CN | 101880640 A | 11/2010 |
| CN | 104740622 A | 7/2015 |
| CN | 105199991 A | 12/2015 |
| WO | 2009/101475 A2 | 8/2009 |

OTHER PUBLICATIONS

Jian-Li et al (Scientific Reports. Dec. 11, 2017 online published. 7: 17291, pp. 1-7).*
Ahmad et al (Vaccine. 30. 2012: 2411-2420).*
Silva et al (Arq. Bras. Med. Vet. Zootec. vol. 53 No. 4 Belo Horizonte Aug. 2001).*
Martinon et al (J. Immunol. Res. vol. 2019. Article ID 3974127, pp. 1-9, May 8, 2019).*
First Office Action dated Jul. 3, 2020, by the State Intellectual Property Office of the Peoples Republic of China in corresponding Chinese Patent Application No. 201910713961.X and an English translation of the Action. (10 pages).
Notification to Grant Patent Right for Invention dated Aug. 26, 2020, by the State Intellectual Property Office of the Peoples Republic of China in corresponding Chinese Patent Application No. 201910713961.X and an English translation of the Notification. (3 pages).

* cited by examiner

*Primary Examiner* — Jennifer E Graser
(74) *Attorney, Agent, or Firm* — Buchanan Ingersoll & Rooney PC

(57) ABSTRACT

A SD-1 strain of *Klebsiella pneumoniae* from mink and its application are disclosed, wherein the collection number of the *Klebsiella pneumoniae* is CGMCC NO: 17901. The *Klebsiella pneumoniae* SD-1 strain can be used for preparing a vaccine. The preferred form of the vaccine is an inactivated vaccine. The SD-1 strain of *Klebsiella pneumoniae* was screened from minks that died after vaccination. Compared with the current *Klebsiella pneumoniae*, the strain has mutated and is a new type of pathogenic strain. Vaccine prepared from the SD-1 strain provides better immune protection for minks.

5 Claims, No Drawings

Specification includes a Sequence Listing.

SEQUENCE LISTING

```
<160> NUMBER OF SEQ ID NOS: 4

<210> SEQ ID NO 1
<211> LENGTH: 360
<212> TYPE: DNA
<213> ORGANISM: Klebsiella pneumoniae

<400> SEQUENCE: 1
actgggctac ctctgcttaa caagacattt gaagcagtaa ttaataaatc aatattgatg      60
aagcacaaaa aaaacataag agtattggct gactgcgggt ttttttattc atccacatgg     120
agagggtaca aaatgttaag atccacatta catatgataa gccaatggac acggcttcat     180
gtttcggggg gggggcggtt tcacctttgc agcaggtgtg cttattacct ttatgttaaa     240
```

-continued

```
atgcaagatc cactaaaaag tattggctca aaactatatc ttgcactctc aaagaaaaat    300
gtactgggaa ttgtaaaaca ttatcctcgg ctaacaaaaa aagaacaatg gatgctgcaa    360

<210> SEQ ID NO 2
<211> LENGTH: 119
<212> TYPE: PRT
<213> ORGANISM: Klebsiella pneumoniae

<400> SEQUENCE: 2

Thr Gly Leu Pro Leu Leu Asn Lys Thr Phe Glu Ala Val Ile Asn Lys
1               5                   10                  15

Ser Ile Leu Met Lys His Lys Lys Asn Ile Arg Val Leu Ala Asp Cys
            20                  25                  30

Gly Phe Phe Tyr Ser Ser Thr Trp Arg Gly Tyr Lys Met Leu Arg Ser
        35                  40                  45

Thr Leu His Met Ile Ser Gln Trp Thr Arg Leu His Val Ser Gly Gly
    50                  55                  60

Gly Arg Phe His Leu Cys Ser Arg Cys Ala Tyr Tyr Leu Tyr Val Lys
65                  70                  75                  80

Met Gln Asp Pro Leu Lys Ser Ile Gly Ser Lys Leu Tyr Leu Ala Leu
                85                  90                  95

Ser Lys Lys Asn Val Leu Gly Ile Val Lys His Tyr Pro Arg Leu Thr
            100                 105                 110

Lys Lys Glu Gln Trp Met Leu
        115

<210> SEQ ID NO 3
<211> LENGTH: 19
<212> TYPE: DNA
<213> ORGANISM: Klebsiella pneumoniae

<400> SEQUENCE: 3
tgattgcatt cgccactgg                                                 19

<210> SEQ ID NO 4
<211> LENGTH: 19
<212> TYPE: DNA
<213> ORGANISM: Klebsiella pneumoniae

<400> SEQUENCE: 4
ggtcaaccca acgatcctg                                                 19
```

KLEBSIELLA PNEUMONIAE FROM MINKS AND ITS APPLICATION

TECHNOLOGY FIELD

The present innovation belongs to the technical field of veterinary biological products, and in particular relates to a *Klebsiella pneumoniae* from mink and its application.

TECHNOLOGY BACKGROUND

Mink farming is a special farming mainly to produce skin. Mink skin is thin, pliable and strong. It is the main raw material for making clothes, collars, hats, cuffs and ornaments. From the perspective of the quality and value, its utilization rate is higher than that of fox skin, raccoon skin and other large-size skins, so it has great potential in the domestic market. The large-size skins such as fox skin and raccoon skin are thicker and longer than mink skin, and are not as gorgeous as mink skin, so they are not suitable for making coats. They are only suitable for making collars, cuffs, shawls and other accessories. Therefore their utilization rate is lower than that of mink skin.

However, in recent years, with the increase in mink prices, the farming volume has become larger and larger, and the farming density has continued to increase, resulting in an increase of diseases, among which, hemorrhagic pneumonia in minks is the most harmful to mink farming. Hemorrhagic pneumonia in minks mainly occurs when the minks' summer hair falls off in autumn. When the minks' summer hair falls off, the hair that has fallen off is flying around in the farm, and the bacteria adhering to the hair can contaminate feed and drinking water at any time and cause infection. The attack of hemorrhagic pneumonia in minks is mainly acute, and infected minks often die without any symptoms. Bloody foam comes out of the mouths and noses of the sick and dead minks. The symptoms of hemorrhagic pneumonia in minks mainly include dyspnea, hemorrhagic pneumonia changes, pulmonary edema, hemorrhagic pathological changes of organs and gastrointestinal mucosal ulcers, and individual mink will also occur increased eye secretions, paw enlargement, etc. Hemorrhagic pneumonia in minks is often endemic, causing greater economic losses to farmers.

When hemorrhagic pneumonia in minks occurs, it is often too late to treat. The commonly used drugs tilmicosin, azithromycin, kanamycin are not effective, and the abuse of antibiotics will make the pathogenic bacteria resistant to drugs, so effective vaccines are needed to prevent it. At present, in the prevention of hemorrhagic pneumonia in minks, most countries mainly use inactivated bacterial vaccine products, that is preparing polyvalent inactivated vaccines by inactivating epidemic serotype strains, which can effectively prevent the disease caused by similar serotype strains.

SUMMARY OF THE INVENTION

The purpose of the present innovation is to provide a *Klebsiella pneumoniae* from mink and its application. The provided *Klebsiella* is a new strain with mutation, and the vaccine prepared by using it can provide more comprehensive protection for minks, thereby making up for the deficiencies of the existing technology.

The *Klebsiella pneumoniae* SD-1 strain of the present innovation was deposited in the China General Microbiological Culture Collection Center, No. 3, Courtyard 1, Beichen West Road, Chaoyang District, Beijing on Jun. 5, 2019, and the collection number is CGMCC NO: 17901.

The *Klebsiella pneumoniae* SD-1 strain of the present innovation is used for preparing vaccine.

The preferred form of the said vaccine is the inactivated vaccine.

The present innovation also provides an inactivated vaccine, which comprises an inactivated antigen and a vaccine adjuvant, wherein the inactivated antigen is inactivated *Klebsiella pneumoniae* (*Klebsiella* sp.) SD-1 strain.

The said vaccine adjuvant is an aqueous vaccine adjuvant, more specifically, aluminum hydroxide gel.

The *Klebsiella pneumoniae* present of the present innovation was screened from minks that died after the vaccination. Compared with the current *Klebsiella pneumoniae*, the strain has mutated and is a new type of mutated pathogenic strain. The said strain is used to prepare the vaccine to provide better immune protection for minks.

DETAILED DESCRIPTION

The present innovation uses the conventional techniques and methods in the fields of genetic engineering and molecular biology, such as MOLECULAR CLONING: the method described in A LABORATORY MANUAL, 3nd Ed. (Sambrook, 2001) and CURRENT PROTOCOLS IN MOLECULAR BIOLOGY (Ausubel, 2003). These general references provide definitions and methods known to those skilled in the field.

The present innovation will be described in detail in combination with the following embodiments.

Embodiment 1: Analysis of Purification and Physicochemical Properties of Isolation of Strains In 2018, the symptoms of hemorrhagic pneumonia in mink appeared in a mink farm in Qingdao, but the affected minks had previously been injected with an officially launched triple inactivated vaccine against hemorrhagic pneumoniae *P. aeruginosa* in minks, *Pasteurella multocida* and *Klebsiella pneumoniae.*

1) Take a dead mink and use a scalpel to aseptically open the chest and abdominal cavity of the sick and dead mink. Cut the liver of the sick and dead mink to fully expose its internal tissues. Dip the contents of the liver with a sterile cotton swab and then carry out gradient dilution on it with normal saline, then make a streak on the LB solid agar medium, and culture the culture dish with bacteria at 37° C. for 10-12 h. Select single bacterial colonies. Culture each single colony on the urinary tract flora chromogenic medium.

2) Strains showing different colors on the chromogenic medium will be inoculated into LB liquid medium as a group of 3 for expanded culture, and then centrifuge it at 4000 rpm to collect bacterial cells. Resuspend the bacterial cells with 0.5% sterile normal saline, and set the bacterial concentration of the strains as $1\times10^7$ CFU/mL by turbidimetric method for injection infection.

4) Carry out inject infection experiments with healthy minks that have been inoculated with the triple inactivated vaccine against hemorrhagic pneumoniae *P. aeruginosa* in minks, *Pasteurella multocida* and *Klebsiella pneumoniae*. Inject 0.2 mL of bacterial suspension of different strains to be screened into the abdominal cavity, and inject 0.5% sterile normal saline, of the same volume into the control group. For the affected minks, the three single colonies in the combined bacterial suspension will be separately tested for injection infection.

Finally, a strain that is blue on the urinary tract flora chromogenic medium is determined. Injection infection shows that it will cause the symptoms of hemorrhagic pneumonia in minks who have been injected with the mink hemorrhagic pneumonia vaccine.

The strain can form grayish white and round raised colonies on the serum LB agar medium. Grain-negative.

Extract the bacterial DNA with a bacterial genomic DNA extraction kit, perform PCR amplification with the 16S rRNA bacterial identification primers, then go through electrophoresis, recovery, cloning and sequencing, and analyze the sequencing results. Send the PCR amplification products to the sequencing company for sequencing. After sequence alignment on NCBI, the 16S rRNA sequence has the highest homology with *Klebsiella*, so it is suspected to belong to *Klebsiella*.

Since the Khe gene can be used as a target gene for identifying *Klebsiella pneumoniae*, primer pairs that amplify the Khe gene are used to detect the genomic DNA of the screened strain. The sequence information of the primer pairs is as follows:

```
Upstream primer:
                              (SEQ ID NO: 3)
5'-TGATTGCATTCGCCACTGG-3'

Downstream primer:
                             ( SEQ ID NO: 4)
5'-GGTCAACCCAACGATCCTG-3'
```

The amplification results show that positive fragments appear in the strain, which is consistent with 16S rRNA, confirming that the screened strain is *Klebsiella pneumoniae* and is named SD-1 strain.

Considering that SD-1 strain will cause disease in minks that have been vaccinated, in order to verify whether the pathogenic gene of SD-1 strain has been mutated, the *Klebsiella pneumoniae* SD-1 strain and pathogenesis-related rmpA gene, uge gene, magA gene, wabG gene, capsular polysaccharide K2 gene are amplified and sequenced. Use EasyPure Quick Gel Extraction Kit to recover PCR products, connect to pEASY-Blunt Cloning vector or pMD18-T Vector (Promega) to transform Trans-5α competent cells, and then sequence after identification. Use DNAMAN software to deduce the amino acid sequence.

Perform amino acid homology comparison of the pathogenesis-related gene fragments with the *Klebsiella pneumoniae* sequences published on GenBank. The results show that the pathogenesis-related uge gene, magA gene, and wabG gene have multiple mutations at the amino acid level, and the nucleotide sequence of rmpA gene is SEQ ID NO: 1 and the amino acid sequence is SEQ ID NO: 2. Compared with what have been reported, the amino acid homology is only 70%, which may be the reason why the immunity of existing *Klebsiella* genes is not good.

```
                                    ( SEQ ID NO: 1)
ACTGGGCTACCTCTGCTTAACAAGACATTTGAAGCAGTAAT

TAATAAATCAATATTGATGAAGCACAAAAAAAACATAAGAG

TATTGGcTGACTGCGGGtTTTTTTATTCATCCACATGGAGA

GGGTACAAAATGTTAAGATCCACATTAcATATGATAAGCCA

ATGGAcAcGGCTTcATGTTTCGGGGGGGGGCGGTTTcACC

TTTGcAGCAGGTGTGcTTATTACcTtTATGTTAAaATGCAA

GATCCACTAAAAAGTATTGGcTcAAAACTATATcTTGCAcT

CTcAAAGAAAAATGTACTGGGAATTGTAAAaCATTATCCtC

GGCTAACAAAAAAAGAACAATGGATGCTGCAA (SEQ ID NO: 2)
TGLPLLNKTFEAVINKSILMKHKKNIRVLADCGFFYSSTWR

GYKMLRSTLHMISQWTRLHVSGGGRFHLCSRCAYYLYVKMQ

DPLKSIGSKLYLALSKKNVLGIVKHYPRLTKKEQWMLQ
```

Embodiment 2: Detection of the Pathogenic Effect of SD-1 Strain

First, inoculate *Klebsiella pneumoniae* SD-1 strain on the LB solid plate medium and cultivate it at 37° C. for 24 hours. Then select single colonies to inoculate into the LB liquid medium, stir it at 37° C. in a ventilated environment and then culture it for 24 h, then centrifuge it at 4000 rpm for 10 min to collect the precipitate, then resuspend the precipitate with sterile normal saline, and count the viable bacteria in the suspension. Prepare for animal injection infection experiments.

Select twenty heads of 30-40 day-old healthy and susceptible minks and randomly divide them into 4 groups with 5 heads in each group. Dilute the fermentation solution of *Klebsiella pneumoniae* SD-1 strain into three different gradients of $1.0 \times 10^6$ CFU, $4.0 \times 10^6$ CFU/ml and $6.0 \times 10^6$ CFU/ml, and inoculate 2.0 ml into each of the minks of a group and inject 2.0 l of sterile normal saline, into each of the minks of another group as a control.

Observe for 7-20 days and record the clinical situation. The results show that most minks in the group injected with the fermentation solution experience clinical symptoms of hemorrhagic pneumonia in minks such as increased body temperature, decreased appetite, abdominal breathing, hemoptysis or red foamy liquid from the nostrils or even death. The body temperature of the minks in the control group does not change significantly, and there are no clinical symptoms or death in the group (Table 1).

TABLE 1

Infectivity of Klebsiella pneumoniae SD-1 Strain

| Group | Number of injections | Challenged viral dosage | Number of challenged bacteria | Number of infected minks |
| --- | --- | --- | --- | --- |
| SD-1 strain | 5 | 2 ml | $1.0 \times 10^6$ CFU | 4/5 incidence |
|  | 5 | 2 ml | $4.0 \times 10^6$ CFU | 5/5 incidence |
|  | 5 | 2 ml | $6.0 \times 10^6$ CFU | 5/5 incidence |
| Control group | 5 | 2 ml | Normal saline 1 | 0/5 incidence |

The above results show that the minimum amount of *Klebsiella pneumoniae* SD-1 strain that can cause the 5/5 incidence of a healthy and susceptible mink 30 to 40 days old is $4.0 \times 10^6$ CFU/ml, which indicates that the strain selected by the present innovation has strong pathogenicity.

Embodiment 3: Preparation of Vaccines Using Klebsiella Pneumoniae SD-1 Strain 1. Preparation of Inactivated Vaccines:

First, inoculate *Klebsiella pneumoniae* SD-1 strain on the LB solid plate medium and cultivate it at 37° C. for 24 hours. Then select single colonies to inoculate into the LB liquid medium, stir it at 37° C. in a ventilated environment and then culture it for 24 h, then add 0.1% formaldehyde solution to the total amount of the bacterial solution, inactivate it for 24 hours, and stir 3 times during this period. Add aluminum hydroxide gel with a volume percentage of 30% into the obtained inactivated bacterial solution to prepare vaccines. Prepare three batches of vaccines in this way.

Vaccine inactivation test: Take and add 100 μl of formaldehyde-inactivated bacterial solution into 3 ml liquid medium, and take three samples per culture and inoculate each sample in three test tubes and observe for five days for inactivated security test, if the liquid medium in the test tubes remains clear without turbidity after five days, it indicates that the prepared vaccines meet the requirements.

The prepared vaccines are tested without bacterial growth according to page 42 of Appendix of *Veterinary Pharmacopoeia of the People's Republic of China* (2010 edition).

Inject the three batches of prepared vaccines into the inner muscles of the hind limbs of healthy minks with three injection volumes of single dose, single dose repeat and overdose. After 10 days of inoculation, the body temperature and appetite of the inoculated minks are normal, there is no swelling and inflammation in the inoculated area, there is no adverse local and systemic immune reactions, and the inoculated minks eat normally, indicating that the vaccines are safe for minks.

2. The Immune Effect of the Vaccines

Randomly divide the 2-3 month-old healthy minks into six groups, 10 heads in each group. There were 40 heads in the vaccine injection groups and 20 in the control groups. Inject 0.2 ml of the $5\times10^7$ cfu/mL mink *Klebsiella* inactivated vaccine prepared in Embodiment 2 into the inner muscles of the hind limbs of each of the 20 minks in the first vaccine injection group. Inject the commercially available triple inactivated vaccine for hemorrhagic pneumonia in mink into the other 20 minks in the second vaccine injection group, and the minks in the control groups are injected with normal saline, only.

Thirty days after inoculation, conduct infection experiments using CMCC (B) 46117, the standard strain of *Klebsiella pneumoniae*, ATCC 13883, the mixed strain of *Klebsiella pneumoniae*, and SD-1 strain, respectively.

Inoculate infected bacteria into the muscles of minks in the experimental groups and the control groups, feed and observe the minks for 7 days, and record the attack and mortality of the minks in each group. The experimental results are shown in Table 1 and Table 2.

TABLE 1

Vaccine Immunization Efficacy Data Sheet for Infection with a Mixed Strain of CMCC (B) 46117 and ATCC 13883 *Klebsiella pneumoniae*

| Group | Number of challenged minks (head) | Survival number (head) | Survival rate (%) |
|---|---|---|---|
| Vaccine group 1 | 10 | 9 | 90 |
| Vaccine group 2 | 10 | 10 | 100 |
| Control group | 10 | 3 | 30 |

TABLE 2

Vaccine Immunization Efficacy Data Sheet for Infection with QDNDSD-1 Strain

| Group | Number of challenged minks (head) | Survival number (head) | Survival rate (%) |
|---|---|---|---|
| Vaccine group 1 | 10 | 10 | 100 |
| Vaccine group 2 | 10 | 6 | 60 |
| Control group | 10 | 2 | 20 |

Results of the above infection experiments show that the inactivated vaccine prepared by the SD-1 strain of the present innovation can provide complete protection against the infection of SD-1 strain. The minks in vaccine group 1 do not show any clinical symptoms and there is no death phenomenon. However, the commercially available vaccine only provides partial protection against infection with the SD-1 strain. Therefore, the vaccine prepared by existing mink *Klebsiella* can not sufficiently cross-protect the mink *Klebsiella* SD-1 strain screened by the present innovation, and combined vaccine is needed to be prepared with the QDNDSD-1 strain to provide more complete protection.

What is claimed is:

1. A vaccine comprising inactivated *Klebsiella pneumonia* strain SD-1 and a vaccine adjuvant, wherein the SD-1 strain of *Klebsiella pneumonia* has been deposited in the China General Microbiological Culture Collection Center with accession number CGMCC NO: 17901.

2. The vaccine according to claim 1, wherein the *Klebsiella pneumonia* comprises the DNA sequence of SEQ ID NO: 1.

3. The vaccine according to claim 1, wherein the vaccine adjuvant is an aqueous vaccine adjuvant.

4. The vaccine according to claim 1, wherein the vaccine adjuvant is aluminum hydroxide gel.

5. The vaccine according to claim 4, wherein the *Klebsiella pneumonia* comprises the DNA sequence of SEQ ID NO: 1.

* * * * *